(12) United States Patent
Hyatt

(10) Patent No.: US 7,696,363 B2
(45) Date of Patent: Apr. 13, 2010

(54) PREPARATION OF FLAVONOID COMPOUNDS

(75) Inventor: John A. Hyatt, Kingsport, TN (US)

(73) Assignee: Yasoo Health Inc., Johnson City, TN (US)

( * ) Notice: Subject to any disclaimer, the term of this patent is extended or adjusted under 35 U.S.C. 154(b) by 471 days.

(21) Appl. No.: 11/566,569

(22) Filed: Dec. 4, 2006

(65) Prior Publication Data

US 2007/0149788 A1    Jun. 28, 2007

Related U.S. Application Data

(60) Provisional application No. 60/741,971, filed on Dec. 2, 2005.

(51) Int. Cl.
*C07D 311/74*    (2006.01)

(52) U.S. Cl. .................. 549/406; 549/399; 549/404
(58) Field of Classification Search ................. 549/406
See application file for complete search history.

(56) References Cited

U.S. PATENT DOCUMENTS 7,488,494 B2 *    2/2009    Heaton et al. ............... 424/439
2005/0143588 A1 *    6/2005    Heaton et al. ............... 549/403

OTHER PUBLICATIONS

Muthyala et al, Biooganic and Medicinal Chemistry, vol. 21, p. 1559-1567 (2004).*

* cited by examiner

*Primary Examiner*—Bernard Dentz
(74) *Attorney, Agent, or Firm*—Donna Russell

(57) ABSTRACT

Disclosed is an improved method for preparing the isoflavonoid compound (+/−)-equol, the method comprising reducing an organic diester of the isoflavone daidzein under hydrogen-transfer conditions using palladium hydroxide catalyst.

7 Claims, No Drawings

PREPARATION OF FLAVONOID COMPOUNDS

CROSS-REFERENCE TO RELATED APPLICATIONS

This application claims the benefit of priority of earlier-filed United States Provisional Patent Application No. 60/741,971, filed Dec. 2, 2005.

FIELD OF THE INVENTION

The invention relates to methods of chemical synthesis. More particularly, the invention relates to methods for synthesizing an isoflavonoid compound.

BACKGROUND OF THE INVENTION

Members of the group of naturally-occurring compounds known collectively as phytoestrogenic isoflavonoids have recently been shown to have significant effects on human health, including antioxidant behavior (Jha et al. 1985), antitiumor activity (Hirano et al. 1989; Hirano et al., 1994), and anti-mutagenic activity (Hartman and Shankel, 1990). Furthermore it has been shown that one member of this compound group, the isoflavonoid compound daidzein, acts synergistically with the anticancer drug tamoxifen in prevention of mammary tumors (Constantinou et al. 2005). It has also been demonstrated that intestinal bacteria present in many, but not all, mammals and humans metabolize daidzein through transformation to the reduction product S-(−)-equol [7-hydroxy-3-(4'-hydroxypphenyl)-chroman] (Wang et al. 2005). Equol is a nonsteroidal estrogen of the isoflavone class. It is thought that daidzein serves merely as a precursor or prodrug to equol, and that equol may be a more generally effective anticancer compound than is daidzein. There is therefore a need for a method of obtaining equol in sufficient quantities for both research and medicinal purposes.

Equol contains a single enantiomeric carbon atom and exists in both R- and S-isomers and as the racemic modification, (+/−)-equol. Methyala et al. (2004) demonstrated that (+/−)-equol can be separated into its two optically pure components through chromatography on an appropriate chiral support. This process is not easily performed, however.

The synthesis of (+/−)-equol was first reported by Wessely and Prillinger in 1939. These workers reduced the readily-available daidzein to racemic equol using a very large amount of a specially-prepared palladium catalyst under conditions of high-pressure hydrogenation. Lamberton et al. reported in 1978 that the catalyst preparation of Wessely and Prillinger was impractical and that the catalyst could not be reused; furthermore, commercial grades of palladium catalysts were ineffective in carrying out this conversion. Lamberton et al. (1978) described the reduction of daidzein diacetate to equol diacetate in good yield using the specially prepared catalyst of Wessely and Prillinger, but in addition to the difficulty of obtaining this catalyst, they discovered that the reaction required 30 g of the catalyst to produce 4.1 g of product. Furthermore, an additional step, saponifying the acetate groups of equol diacetate, was necessary to obtain equol.

Wahala and Hase (1989) attempted to reduce daidzein under the condition of palladium-catalyzed hydrogen-transfer reduction rather than pressure hydrogenation. Using ammonium formate as the hydrogen donor and ordinary commercially available palladium/charcoal catalyst, they obtained only partially reduced isoflavanones and isoflavanols, and no equol. However in 2004 Muthyala et al. reported that hydrogen-transfer reduction using ammonium formate in acetic acid and palladium hydroxide on carbon catalyst ("Pearlman's catalyst") converted daidzein into equol in 61% yield. In order to obtain equol in this yield it was necessary to chromatograph the initially-obtained brown oily crude product to remove nearly 40% of undesirable impurities.

Using methods existing in the art, equol is generally considered to be a relatively expensive compound (e.g., $275 per 5 mg sample). Because it may be effective for a variety of therapeutic applications such as cancer therapy, treatment of benign prostate hyperplasia, and hormone-mediated conditions such as bone loss, hair loss, and abnormal hair growth, for example, a need exists for methods of synthesizing biologically active equol to produce an affordable product for therapeutic use.

SUMMARY OF THE INVENTION

The present invention relates to a method for synthesizing a phytoestrogenic isoflavonoid compound of formula (I)

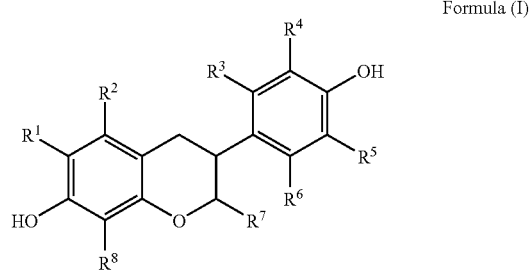

Formula (I)

wherein $R^1$, $R^2$, $R^3$, $R^4$, $R^5$, $R^6$, $R^7$ and $R^8$ are independently hydrogen, $C_1$ to $C_{18}$ straight chain alkyl, $C_1$ to $C_{18}$ branched alkyl, phenyl or substituted aryl, halogen, hydroxyl, alkoxyl, acetoxy, or acetamido, the method comprising reducing under hydrogen-transfer conditions an isoflavone diester of Formula (II)

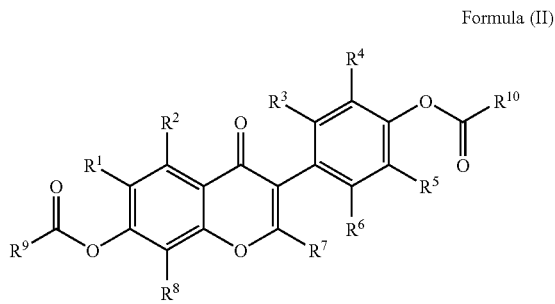

Formula (II)

wherein $R^9$ and $R^{10}$ are independently hydrogen, $C_1$ to $C_{18}$ straight chain alkyl, $C_1$ to $C_{18}$ branched alkyl, phenyl or substituted aryl, halogen, hydroxyl, alkoxyl, acetoxy, or acetamido; and $R^1$, $R^2$, $R^3$, $R^4$, $R^5$, $R^6$, $R^7$, and $R^8$ are independently hydrogen, substituted or unsubsidized $C_1$ to $C_{18}$ straight-chain alkyl, substituted or unsubstituted $C_1$ to $C_{18}$ branched alkyl, cycloalkyl, phenyl, substituted aryl, halogen, hydroxyl, alkoxyl, alkoxyl, acetoxy, or acetamido.

The invention also provides a method for producing (+/−)-equol, the method comprising reducing the diacetate of daidzein (Formula III)

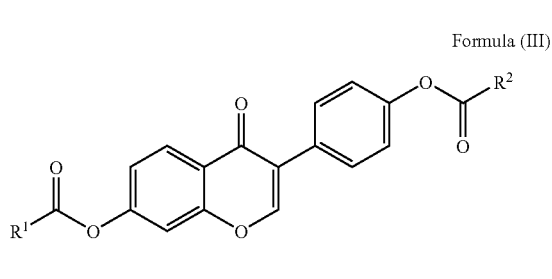

Formula (III)

by hydrogen-transfer reduction in the presence of a palladium hydrogen hydroxide on carbon catalyst and adding ammonium formate as hydrogen donor and acetic acid as a solvent.

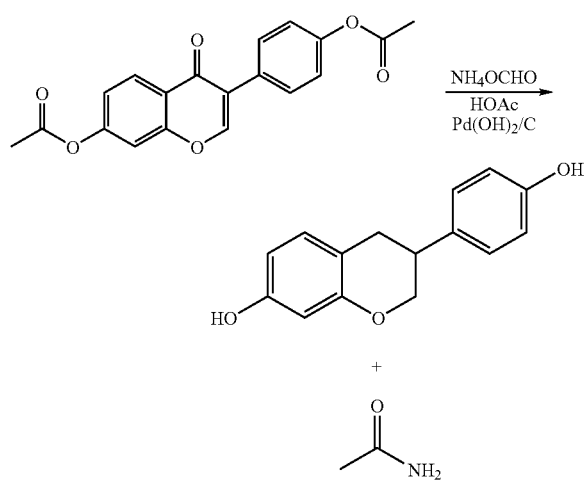

DETAILED DESCRIPTION OF THE INVENTION

The present invention primarily relates to a process for the preparation of the isoflavonoid compound (+/−)-equol and closely related analogs and homologs of equol having Formula (I)

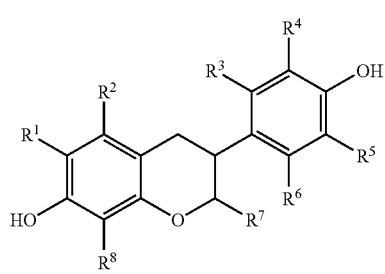

Formula (I)

wherein $R^1$, $R^2$, $R^3$, $R^4$, $R^5$, $R^6$, $R^7$, and $R^8$ are independently hydrogen, $C_1$ to $C_{18}$ straight chain alkyl, $C_1$ to $C_{18}$ branched alkyl, phenyl, or substituted aryl, halogen, hydroxyl, alkoxyl, acetoxy, or acetamido. Equol and isoflavonoid analogs and homologs of equol having Formula (I) may be produced by the method herein described by the use of a compound of Formula (II) (a diacetate) as a starting material.

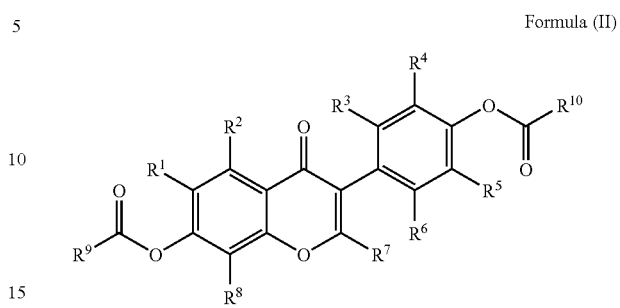

Formula (II)

The inventor has discovered that a desired (+/−)-equol compound can be obtained in a single step in significantly higher yield by reduction of daidzein diacetate, instead of free daidzein, under the reduction conditions prescribed by Muthyala et al. Furthermore, the (+/−)-equol obtained by this novel method is of a sufficiently high purity as to render further purification by chromatography or recrystallization unnecessary. The process of the invention comprises reacting an organic diester of daidzein or a closely related analog or homolog with ammonium formate in a solvent consisting of an aliphatic carboxylic acid, in the presence of a catalytic quantity of carbon-supported palladium hydroxide ("Pearlman's catalyst").

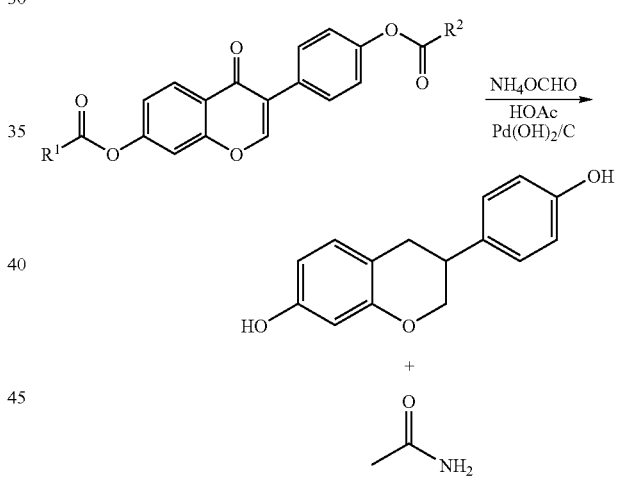

The organic diester of daidzein which is used as the starting material in the process of the present invention is represented by Formula (III) below:

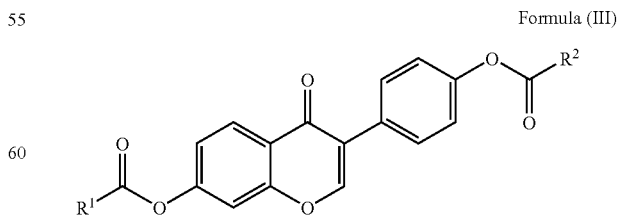

Formula (III)

where $R^1$ and $R^2$ independently represent hydrogen, a $C_1$ to $C_{18}$ straight, branched, or cyclic alkyl, or phenyl. The one or more alkyl groups of Formula (III) may additionally be optionally substituted with, for example, methyl, ethyl, n-propyl, isopropyl, n-butyl, isobutyl, and/or cyclohexyl.

The conversion of the organic diester of daidzein (or a closely related analog or homolog) is conducted under conditions known to effect hydrogen-transfer reduction. The use of ammonium formate as a hydrogen-transfer agent is well known in the art. (see, for example, Ram and Ehrenkaufer (1988)). In the method of the present invention the amount of ammonium formate can range from a three-fold to a twenty-fold molar excess with respect to the amount of daidzein ester being reduced. The amount to be use is preferably in the range of from about 8- to about 20-fold molar excess, and most preferably from about 10-fold to about 15-fold excess.

The process of the present invention should be conducted in the presence of a solvent. Suitable solvents include lower aliphatic carboxylic acids such as formic, acetic, propionic, butryic, and isobutyric acids. In one embodiment acetic acid may be used as the solvent. The amount of solvent employed can range from about 5- to about 50-fold excess by weight with respect to the amount of daidzein diester being reduced. The amount used is preferably in the range of from about 10- to about 15-fold with respect to the daidzein diester, and more preferably about 15-fold. The reaction can be carried out at temperatures ranging from room temperature (from about 15° C. to about 20° C.) to about 125° C., and may be carried out at or near the reflux temperature of acetic acid, or about 90° C. to about 117° C.

A catalyst that may be used in the method of the present invention is commercially available Pearlman's catalyst, which generally may be described as about 10 wt % of palladium hydroxide on carbon support, generally stored in water-wet form (Pearlman 1967). The amount of catalyst to be used in the present process can vary from about 10% to about 85% (wet weight) with respect to the weight of daidzein diester being reduced. Use of from about 25% to about 75% by weight of catalyst gives a reaction time on the order of 1-2 hours. The used catalyst recovered from the hydrogen-transfer reduction step may be re-used in a similar subsequent reaction.

The product of the reaction may be recovered by methods well known in the art, typically by filtration to remove spent catalyst followed by aqueous drown-out or evaporation to remove the solvent. It may be desirable to employ a second solvent such as an aliphatic ester of the carboxylic acid solvent to aid filtration and extraction of the product. Ethyl acetate provides a very effective co-solvent to aid filtration and extraction of the product. Ethyl acetate provides a very effective co-solvent for use in the method.

The product of the reaction carried out by the method of the present invention is equol, not an organic diester of equol. Since the starting material is a diester of daidzein, removal of the ester groups occurs during the reaction. The method of the invention therefore provides a much higher yield and purity of equol than is obtained if daidzein itself is reduced under our reaction conditions.

While not being bound by theory, the inventor believes that the removal of ester groups takes place through aminolysis of the ester groups by action of the ammonium ions from the ammonium formate reducing agent, and that this takes place concomitant with, or immediately after, the reduction of the enone functionality of the daidzein diester. This was ultimately demonstrated by the isolation of acetamide as a by-product when daidzein diacetate was reduced under the described conditions in the inventor's laboratory.

Although this invention is primarily directed toward the preparation of equol, those skilled in the art will realize that the method described herein may be used for the synthesis of similar compounds bearing additional substituents. Such analogs and homologs of equol would be prepared from suitably modified analogs or homologs of daidzein. An example of such a use of the method is represented by the following equation

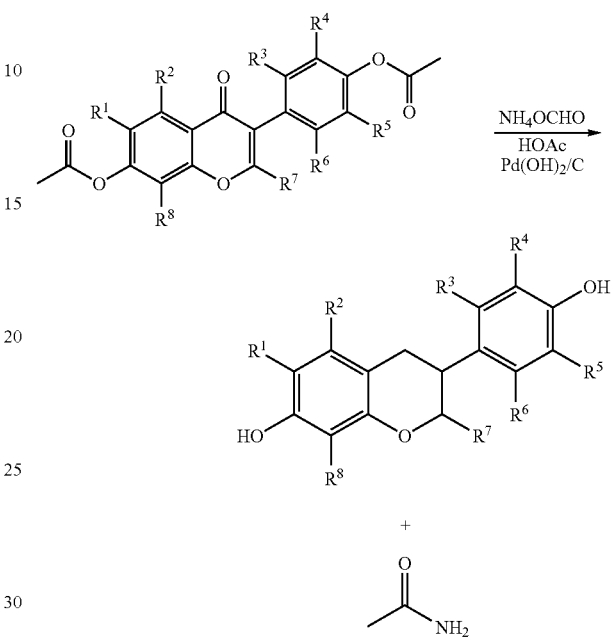

where, $R^1$-$R^8$ may be optionally and independently substituted with hydrogen, $C_1$ to $C_{18}$ straight-chain alkyl, $C_1$ to $C_{18}$ branched alkyl, phenyl or substituted aryl, halogen, hydroxyl, alkoxyl, acetoxy, acetamido, or functionally similar substituents.

EXAMPLES

Preparation of (+/−)-Equol From Diaidzein Diacetate

A 250-ml round bottom flask was equipped with reflux condenser, heating mantle, and magnetic stirrer, and was charged with 8.15 grams of daidzein diacetate (0.024 mole), 100 ml of acetic acid, 20 grams of ammonium formate (31 mole), and 5.0 grams of commercial Pearlman's catalyst. The mixture was stirred at relfux for 1.4 hours, at which time thin-layer chromatographic analysis indicated consumption of the starting material. The reaction mixture was cooled to room temperature, diluted with 100 ml of ethyl acetate, and filtered through a pad of diatomaceous earth filter aid. The resulting clear filtrate was poured into about 500 ml of water and shaken. The layers were allowed to separate and the top organic layer was separated, washed with water and then with 5% aqueous sodium bicarbonate solution to remove residual acetic acid. (The acetamide by-product is extracted into the water layers during this procedure.) The resulting clear solution was stripped of ethyl acetate under reduced pressure to give an off-white solid product. This material was triturated with about 15 ml of chloroform and the resulting white solid product filtered off and air-dried to afford 4.85 grams of (+/−)-equol (83.2% yield). The product was analyzed by IR and proton NMR spectroscopy and found to be of greater then 95% purity.

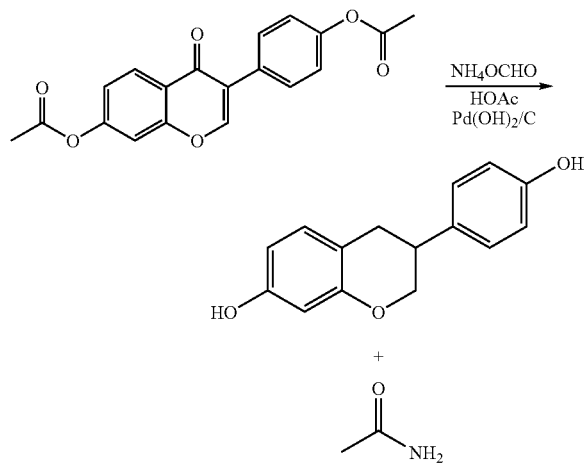

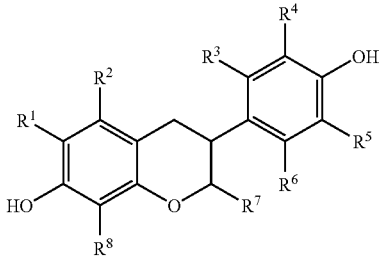

Preparation of Equol by Reduction of Free Daidzein
(for Comparison)

A flask was charged with 2.00 grams of daidzein, 4.8 grams of ammonium formate, 15 ml of acetic acid, and 1.5 grams of commercial Pearlman's catalyst. The resulting mixture was refluxed for 1.25 hr, cooled, and diluted with 50 ml of ethyl acetate. The mixture was filtered (filter-aid) and partitioned with 250 ml of water. The organic phase, which was dark in color, was washed with water, 5% sodium bicarbonate solution, dried, and stripped of solvent under reduced pressure. There was obtained about 1.7 grams of a dark oily substance which was subjected to preparative-scale column chromatography on silica gel. Elution with 1% methanol in chloroform allowed isolation of the major component of the mixture as a light brown oil which was crystallized from chloroform when seeded with authentic equol. The final product was a yellow solid which weighted 0.91 gram (48% yield) and was identified as equol of about 95% purity from its proton NMR spectrum.

Although the invention has been described in detail with particular reference to a preferred embodiment thereof, it will be understood that a variety of variations and modifications may be made while still remaining within the spirit and scope of the invention.

REFERENCES

1. Jha, H., G. Recklinghausen, and F. Zilliken, *Biochem. Pharmacol.* 34, 1367-1369 (1985).
2. Hirano, T., K. Oka, and M. Akiba, *Res. Commun. Chem. Pathol. Pharmacol.* 64, 69-78 (1989).
3. Hirano, T., M. Gotoh, and K. Oka, *Life Sci.* 55, 1061-1069 (1994).
4. Hartman, P. and D. Shanke, *Environ. Mol. Mutagen.* 15, 145-182 (1990).
5. Constantinou, A., B. White, D. Tonetti, Y. Yang, W. Liang, W. Li, and R. van Breeman, *Eur. J. Cancer* 41, 647-654 (2005).
6. Wang, X., H. Hur, J. Lee, K. Kim, and S. Kim, Applied Environ. Microbiology 71, 214-219 (2005).
7. Muthyala, R., Y. Ju, S. Sheng, L. Williams, D. Doerge, B. Katzenellenbogen, W. Helferich, and J. Katzenellenbogen, *Bioorg. Med. Chem.* 12, 1559-1567 (2004).
8. Wessely, F. and F. Prillinger, *Chem Ber.* 72 B, 629 (1939).
9. Lamberton, J., H. Suarez, and K. Watson, *Aust. J. Chem.* 31, 455-457 (1978).
10. Wahala, K. and T. Hase, *Heterocycles* 28, 183-186 (1989).
11. Ram, S. and R. Ehrenkaufer, *Synthesis* 1988, 91-95.
12. Pearlman, W., *Tetrahedron Lett.* 29, 1663-1664 (1967).

What is claimed is:

1. A method for synthesizing a phytoestrogenic isoflavonoid compound of Formula (I)

Formula (I)

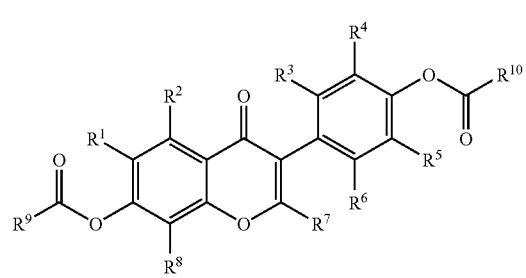

wherein $R^1$, $R^2$, $R^3$, $R^4$, $R^5$, $R^6$, $R^7$, and $R^8$ are independently hydrogen, $C_1$ and $C_{18}$ straight chain alkyl, $C_1$ to $C_{18}$ branched alkyl, phenyl or substituted aryl, halogen, hydroxyl, alkoxyl, acetoxy, or acetamido, the method comprising reducing under hydrogen-transfer conditions an isoflavone diester of Formula (II)

Formula (II)

wherein $R^9$ and $R^{10}$ are independently hydrogen, $C_1$ to $C_{18}$ straight chain alkyl, $C_1$ to $C_{18}$ branched alkyl, phenyl, or substituted aryl, halogen, hydroxyl, alkoxyl, acetoxy, or acetamido; and $R^1$, $R^2$, $R^3$, $R^4$, $R^5$, $R^6$, $R^7$, and $R^8$ are independently hydrogen, substituted or unsubstituted $C_1$ to $C_{18}$ straight-chain alkyl, substituted or unsubstituted $C_1$ to $C_{18}$ branched alkyl, cycloalkyl, phenyl, substituted aryl, halogen, hydroxyl, alkoxyl, acetoxy, or acetamido.

2. The methods of claim 1 wherein the step of reducing is performed by the addition of Pearlman's catalyst.

3. The method of claim 1 further comprising adding a hydrogen-transfer hydrogen donor.

4. The method of claim 3 wherein the hydrogen-transfer hydrogen donor is chosen from the group consisting of hydrazine, hydrazine hydrate, ammonium formate, or combinations thereof.

5. The method of claim 4 wherein the hydrogen-transfer hydrogen donor is ammonium formate.

6. The method of claim 1 further comprising adding a solvent comprising at least one $C_1$ to $C_6$ straight- or branched-chain aliphatic carboxylic acid.

7. The method of claim 6 wherein the solvent is acetic acid.

* * * * *